(12) United States Patent
Leitner et al.

(10) Patent No.: US 8,846,970 B2
(45) Date of Patent: Sep. 30, 2014

(54) METAL CARBAMATES FORMED FROM TOLYLENEDIAMINES

(71) Applicant: BASF SE, Ludwigshafen (DE)

(72) Inventors: Andreas Leitner, Pittsburgh, PA (US); Robert Baumann, Mannheim (DE); Wolfgang Siegel, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/896,416

(22) Filed: May 17, 2013

(65) Prior Publication Data

US 2013/0231495 A1 Sep. 5, 2013

Related U.S. Application Data

(62) Division of application No. 12/920,224, filed as application No. PCT/EP2009/053170 on Mar. 18, 2009, now Pat. No. 8,481,777.

(30) Foreign Application Priority Data

Mar. 18, 2008 (EP) .................. 08152943

(51) Int. Cl.
- *C07C 261/00* (2006.01)
- *C07C 269/00* (2006.01)
- *C07C 271/00* (2006.01)
- *C07C 269/04* (2006.01)
- *C07C 271/28* (2006.01)
- *C07C 269/06* (2006.01)

(52) U.S. Cl.
CPC ............ *C07C 269/04* (2013.01); *C07C 271/28* (2013.01); *C07C 269/06* (2013.01)
USPC ...................................... 560/25

(58) Field of Classification Search
CPC .. C07C 269/06; C07C 269/04; C07C 271/58; C07C 271/52
See application file for complete search history.

(56) References Cited

U.S. PATENT DOCUMENTS

| | | | |
|---|---|---|---|
| 3,763,217 A | 10/1973 | Brill | |
| 4,268,683 A | 5/1981 | Gurgiolo | |
| 4,268,684 A | 5/1981 | Gurgiolo | |
| 4,395,565 A | 7/1983 | Romano et al. | |
| 4,550,188 A | 10/1985 | Frulla et al. | |

FOREIGN PATENT DOCUMENTS

| | | |
|---|---|---|
| DE | 32 02 690 | 8/1982 |
| EP | 0000815 | 2/1979 |
| EP | 0 048 371 | 3/1982 |
| EP | 0 391 473 | 10/1990 |
| WO | 98/55451 | 12/1998 |
| WO | 98/56758 | 12/1998 |
| WO | 2007/015852 | 2/2007 |

OTHER PUBLICATIONS

Cong, et al., Hebei Gongye Daxue Xuebao, vol. 29, No. 1, p. 62 (2000).
Internal Search Report issued Jul. 30, 2009 in PCT/EP09/053170 filed Mar. 18, 2009.

*Primary Examiner* — Rosalynd Keys
*Assistant Examiner* — Jennifer C Sawyer
(74) *Attorney, Agent, or Firm* — Oblon, Spivak, McClelland, Maier & Neustadt, L.L.P.

(57) ABSTRACT

The invention provides metal carbamates of the general formula (I)

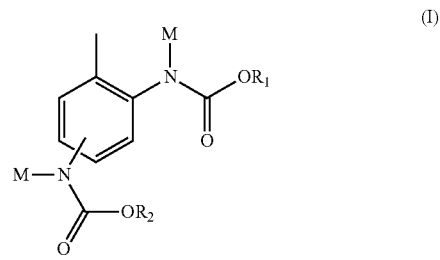

where R1 and R2 are the same or different and are each an alkyl group having 1-18 carbon atoms and M is an alkali metal atom.

10 Claims, No Drawings

METAL CARBAMATES FORMED FROM TOLYLENEDIAMINES

This application is a divisional of U.S. application Ser. No. 12/920,224 filed Aug. 30, 2010, which is a National Stage of PCT/EP2009/053170 filed Mar. 18, 2009, both of which are incorporated herein by reference. This application also claims the benefit of EP 08152943.0 filed Mar. 18, 2008.

DESCRIPTION

The invention provides metal carbamates formed from tolylenediamines and a process for preparing them.

Carbamates have been known for a long time. They are prepared typically by reacting aromatic amines with stoichiometric amounts of a base and an organic carbonate.

For the preparation of carbamates, a series of processes is known.

In these processes, for example, Lewis acids, such as uranium salts (U.S. Pat. No. 3,763,217), aluminum turnings with iodine and Hg promoters (U.S. Pat. No. 4,550,188), zinc salts, iron salts, antimony salts and tin salts (U.S. Pat. Nos. 4,268,683, 4,268,684, EP 391473), are used as catalysts.

A disadvantage for the industrial use of these processes are the sometimes low conversions, low selectivities or both.

High selectivities and yields are obtained, for example, in processes catalyzed with Lewis acids (Pb salts as catalysts), when a high excess of dialkyl carbonate (amine:carbonate 1:20) is used (WO 98/55451, WO 98/56758). The high excess of dialkyl carbonate leads to large recycle streams.

In other cases, high yields of urethane can be achieved when the urea formed in the urethanization is redissociated thermally to the corresponding urethane in an additional reaction (EP 048371 (catalysts: lead salts, titanium salts, zinc salts and zirconium salts), EP 391473 (catalyst: Zn salts)). The redissociation requires an additional, energy-intensive step.

A further disadvantage in the case of use of Lewis acids as homogeneous catalysts is the catalyst residues which remain in the product and can be removed only incompletely.

WO 2007/015852 describes the use of Lewis acidic heterogeneous catalysts for the urethanization of aromatic amines. This dispenses with a complicated removal of a homogeneous catalyst. The resulting conversions are too low for industrial scale applications and decrease together with the selectivity with increasing lifetime of the heterogeneous catalyst.

It is also known that urethanes can be prepared from aromatic amines using basic compounds, for example, alkali metal or alkaline earth metal alkoxides.

DE 3202690 describes the preparation of aromatic urethanes by reaction of aniline and dialkyl carbonates in the presence of a small amount of a metal alkoxide as a catalyst. The conversions described in the examples are incomplete and the selectivities achieved are insufficient for an industrial application.

Journal of Organic Chemistry, 2005, 70, 2219-2224 describes the reaction of aniline with a large excess of dimethyl carbonate (40-fold excess) in the presence of an excess of base such as sodium methoxide (NaOMe) or potassium tert-butoxide (KOtBu). With NaOMe, a selectivity of 67% after a reaction time of 210 min was obtained. With KOtBu, a selectivity after 1 min of 100% is described, which, however, declines to 60% through formation of the N-methylcarbanilate by-product with increasing reaction time. Conversions and isolated yields were not described.

N-arylcarbamates can be converted to isocyanates. Such processes are common knowledge. This procedure allows diisocyanates to be prepared by a phosgene-free route. Such processes are used to prepare aliphatic diisocyanates in particular.

In the case of aromatic diisocyanates, preparation by a phosgene-free process is difficult, since a series of side reactions proceed owing to the high reactivity of the aromatic compounds. However, it would be desirable if aromatic diisocyanates, which are industrially of great significance, were also preparable by phosgene-free processes.

It was an object of the present invention to find a simple means of providing starting materials for the preparation of aromatic diisocyanates by a phosgene-free process, which can be prepared with a high selectivity, a high yield and with high purity.

It has been found that, surprisingly, it is possible to isolate metal carbamates based on tolylenediamine in pure form. After reaction with protic compounds, especially with alcohols or preferably with water, these can be converted to the corresponding diurethane (TDU) and, in a subsequent step, by thermal cleavage to tolylene diisocyanate (TDI).

The invention accordingly provides metal carbamates of the general formula (I)

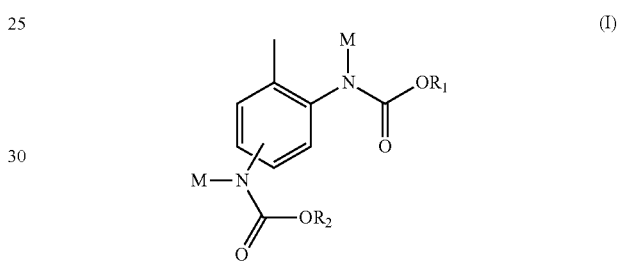

where R1 and R2 are the same or different and are each an alkyl group having 1-18 carbon atoms
and M is an alkali metal atom.

Particular preference is given to alkyl groups having 2-7 carbon atoms, which may be branched, unbranched or cyclic, especially branched or unbranched.

In a preferred embodiment of the invention the R1 and R2 groups are identical.

The invention further provides a process for preparing metal carbamates of the general formula (I) by reacting
a) tolylenediamine with
b) an alkyl carbonate of the general formula (II)

where R1 and R2 are each as defined above and
c) a metal compound of the general formula (III)

where
M is an alkali metal atom,
R3 is the same as R1 and R2, is an amide or an alkylsilazide and
n is equal to 1.

In one embodiment of the invention the alkyl chain R1 and/or R2 is modified with heteroatoms. The heteroatoms may be halogen atoms, preferably fluorine atoms and/or chlorine atoms, more preferably fluorine atoms. In another embodiment, the heteroatoms are oxygen atoms. These are preferably present in the form of ether groups.

R1 and/or R2 is preferably an ethyl, propyl, butyl, 2-methylpropyl, 3-methylbutyl, n-pentyl, 2-methoxyethyl, 2-ethoxyethyl or a 2,2,2-trifluoroethyl group.

R1 and R2 are more preferably identical. This has the advantage that, in the course of preparation of the inventive products (I) and in the course of any further processing to urethanes and conversion thereof to isocyanates, fewer products are in the process.

The compounds of the general formula (I) are solid at room temperature and can be removed from the reaction solution without any problem and in high purity. If required, they can be purified in a further process step.

The compounds of the general formula (I) are prepared, as described above, by reaction of components a), b) and c).

The tolylenediamine used may be any isomers in any mixing ratios. Preference is given to using 2,4-TDA and 2,6-TDA. It is possible to use the pure isomers, preference being given to the pure 2,4-isomer. Also preferred are mixtures of the two isomers with a content of 2,4-TDA of 80% and those with a content of 2,4-TDA of 65%.

In a preferred embodiment of the invention, the dialkyl carbonates b) are selected from the group comprising diethyl carbonate, di-n-propyl carbonate, di-n-butyl carbonate, di-2-methylpropyl carbonate, di-3-methylbutyl carbonate, di-n-pentyl carbonate, bis-2-methoxyethyl carbonate, bis-2-ethoxyethyl carbonate, bis-2,2,2-trifluoroethyl carbonate.

The metal compound c) preferably comprises basic organic metal compounds, especially compounds of alkali metals. They may, for example, be compounds comprising nitrogen atoms, for example amides, such as sodium amide or compounds comprising silicon atoms and nitrogen atoms, for example lithium hexamethyldisilazide.

The base more preferably comprises the alkoxides of alkali metals.

The alkali metal M is preferably lithium, sodium or potassium. The alcohol radicals preferably corresponds to those of the alkyl carbonates of the general formula (II) used.

The compounds of the general formula (I) are prepared preferably under standard pressure at temperatures between 100 and 150° C. The yield of the process is between 95-100%.

In the reaction, the ratio of carbonate groups to amino groups is from 1:1 to 10:1, more preferably from 2:1 to 3:1.

The metal compound c) is preferably used in a stoichiometric amount, more preferably in a molar ratio of 1:1, based on the amino groups, i.e. in a ratio of about one mole of base per amino group.

The inventive metal carbamates may, as described, be converted to pure TDU by protonation with water.

The fact that a simple process would be able to prepare pure metal carbamates and the object of the invention would thus be achieved was not foreseeable to the person skilled in the art.

It was also unnecessary to work with a high excess of component b). In spite of the different reactivity of the two amino groups of the TDA, there was homogeneous conversion of the two amino groups.

The invention will be illustrated in detail by the example which follows.

EXAMPLE 22.4 g (0.13 mol) of diisobutyl carbonate, 3.9 g (0.032 mol) of 2,4-TDA and 6.5 g (0.064 mol) of sodium isobutoxide were weighed successively into a 250 ml four-neck flask equipped with stirrer, internal thermometer and argon supply, which was immersed into an oil bath heated to 120° C. Analysis by thin-layer chromatography after 30 min showed quantitative conversion. The volatile components were drawn off under reduced pressure. Beige crystals (11.5 g) of sodium carbamate were obtained with a yield of 98%.

The invention claimed is:

1. A process for preparing tolylenediurethane, which comprises reacting a metal carbamate of the following general formula (I) with water

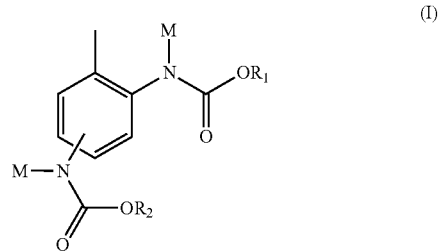

where R1 and R2 are the same or different and are each an alkyl group having 1 to 18 carbon atoms, the alkyl group optionally comprising one or more heteroatoms, and M is an alkali metal.

2. The process according to claim 1, wherein the alkyl groups R1 and R2 each comprise 2-18 carbon atoms in the chain.

3. The process according to claim 1, wherein the alkyl groups R1 and R2 each comprise 2-7 carbon atoms in the chain.

4. The process according to claim 1, wherein the alkyl groups R1 and R2 are selected from the group consisting of an ethyl, propyl, butyl, 2-methylpropyl, 3-methylbutyl, n-pentyl, 2-methoxyethyl, 2-ethoxyethyl and a 2,2,2-trifluoroethyl group.

5. The process according to claim 1, wherein the alkyl groups comprise one or more heteroatoms.

6. The process according to claim 1, wherein the alkyl groups comprise one or more oxygen atoms.

7. The process according to claim 1, wherein no heteroatoms are present in R1 and R2.

8. The process according to claim 1, wherein R1 and R2 are identical.

9. The process according to claim 1, wherein R1 and R2 are branched or unbranched.

10. The process according to claim 1, wherein the metal carbamate is solid at room temperature.

* * * * *